(12) United States Patent
Loper

(10) Patent No.: US 8,575,390 B2
(45) Date of Patent: Nov. 5, 2013

(54) BRANCHED SUCCINIMIDE DISPERSANT COMPOUNDS AND METHODS OF MAKING THE COMPOUNDS

(75) Inventor: John T. Loper, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 441 days.

(21) Appl. No.: 12/974,824

(22) Filed: Dec. 21, 2010

(65) Prior Publication Data

US 2011/0118479 A1    May 19, 2011

Related U.S. Application Data

(62) Division of application No. 11/548,151, filed on Oct. 10, 2006, now Pat. No. 7,875,747.

(51) Int. Cl.
*C07C 231/02*  (2006.01)
*C07C 237/06*  (2006.01)

(52) U.S. Cl.
USPC .......................................... 564/153; 564/136

(58) Field of Classification Search
None
See application file for complete search history.

(56) References Cited

U.S. PATENT DOCUMENTS

| | | | |
|---|---|---|---|
| 3,630,904 A | 12/1971 | Musser et al. | |
| 4,548,724 A | 10/1985 | Karol et al. | |
| 4,948,386 A | 8/1990 | Sung et al. | |
| 4,971,598 A | 11/1990 | Andress et al. | |
| 5,256,325 A | 10/1993 | Emert et al. | |
| 2005/0175543 A1* | 8/2005 | Aime et al. | 424/9.365 |

FOREIGN PATENT DOCUMENTS

FR        2012253        3/1970

\* cited by examiner

*Primary Examiner* — Yevegeny Valenrod
(74) *Attorney, Agent, or Firm* — Luedeka Neely Group, P.C.

(57) ABSTRACT

In accordance with the disclosure, one aspect of the present application is directed to a dispersant compound comprising the reaction product of (i) a hydrocarbyl carbonyl compound, (ii) a polycarbonyl compound having at least three carbonyl acylating functions, and (iii) a primary amine moiety of a polyamine. Methods of making and methods of using the dispersant compound are also disclosed.

10 Claims, No Drawings

BRANCHED SUCCINIMIDE DISPERSANT COMPOUNDS AND METHODS OF MAKING THE COMPOUNDS

RELATED APPLICATIONS

The present application claims the benefit of priority to U.S. NonProvisional patent application Ser. No. 11/548,151 filed on Oct. 10, 2006, the specification and claims of which are herein incorporated by reference.

DESCRIPTION OF THE DISCLOSURE

1. Field of the Disclosure

The present application is directed to dispersant compounds and methods for making the dispersant compounds, and more specifically, to dispersant compounds that can be employed in fuel and lubricant compositions.

2. Background of the Disclosure

Considerable effort has been expended to develop chemical products as dispersant additives for internal combustion engines. Oil-soluble dispersants for lubricating oil have been developed to control deposit and varnish formation, and to keep sludge and other solid matter, such as oxidized base oil, in suspension in the lubricating oil. Dispersants, when added to hydrocarbon fuels employed in the engines, effectively reduce deposit formation that ordinarily occurs in carburetor ports, throttle bodies, venturies, intake ports and intake valves. The reduction of these deposit levels has resulted in increased engine efficiency and a reduction in the level of hydrocarbon and carbon monoxide emissions.

Despite the advances in the use of dispersants as oil and fuel additives, there remains a need for continued improvements in the ability of dispersants to suspend sludge and/or disperse particulates. Thus, novel compounds exhibiting improved dispersant characteristics are desired.

SUMMARY OF THE DISCLOSURE

In accordance with the disclosure, one aspect of the present application is directed to a dispersant compound comprising the reaction product of (i) a hydrocarbyl carbonyl compound, (ii) a polycarbonyl compound having at least three carbonyl acylating functions, and (iii) a primary amine moiety of a polyamine.

Another aspect of the present application is directed to a process for forming a dispersant compound. The process comprises reacting a polycarbonyl compound having at least three carbonyl functions with a primary amine moiety of a polyamine to form a polyamine polyamide intermediate. The intermediate is reacted with a hydrocarbyl carbonyl compound.

Another aspect of the present application is directed to a polyamine polyamide intermediate compound formed by reacting a polycarbonyl compound having at least three carbonyl functions with a primary amine moiety of a polyamine.

Another aspect of the present application is directed to a polyamine polyamide compound of formula III,

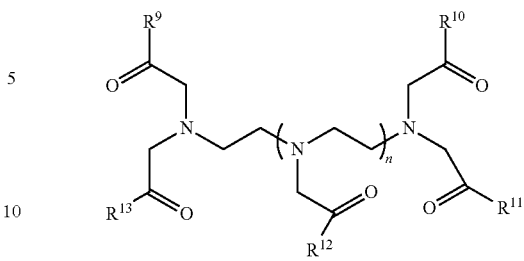

where n ranges from 0 to 10, and $R^9$, $R^{10}$, $R^{11}$, $R^{12}$ and $R^{13}$ are independently chosen from OH, a polyamine group, or a salt of the polyamine group, with the proviso that at least one of $R^9$, $R^{10}$, $R^{11}$, $R^{12}$ and $R^{13}$ is a polyamine group.

Another aspect of the present application is directed to a method of forming a polyamine polyamide intermediate compound. The method comprises reacting a polycarbonyl compound having at least three carbonyl acylating functions with a primary amine moiety of a polyamine.

Another aspect of the present application is directed to a process for forming a dispersant compound. The process comprises reacting a hydrocarbyl carbonyl compound with a primary amine moiety of a polyamine to form a mono-succinimide amine intermediate. The mono-succinimide amine intermediate is reacted with a a polycarbonyl compound having at least three carbonyl functions.

Another aspect of the present application is directed to a polyamine polyamide succinimide of formula VI:

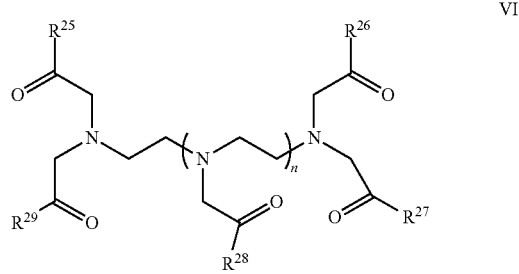

wherein n ranges from 0 to 10, and $R^{25}$, $R^{26}$, $R^{27}$, $R^{28}$ and $R^{29}$ are independently chosen from a polyamine succinimide group or a polyamine succinimide group salt, with the proviso that at least $R^{25}$, $R^{26}$, $R^{27}$, $R^{28}$ and $R^{29}$ is a polyamine succinimide group.

Another aspect of the present application is directed to a lubricating composition comprising a base oil; and a dispersant compound of the present application.

Another aspect of the present application is directed to a method of reducing deposits on a lubricated surface, the method comprising lubricating the surface with a lubricating composition of the present application, wherein a dispersant compound of the present application is present in the lubricating composition in an amount sufficient to reduce the amount of deposits on the lubricated surface, as compared to the amount of deposits on the surface subjected to the same operating conditions and lubricated with the same lubricant composition except that the composition is devoid of the dispersant compound.

Another aspect of the present application is directed to a method for improving the suspension of sludge comprising providing to a combustion system a lubricating composition of the present application, wherein the dispersant compounds are present in an amount sufficient to maintain at least some sludge in suspension in the base oil for a period of time longer than if the base oil did not contain the dispersant compounds.

Another aspect of the present application is directed to a lubricant additive package composition comprising a diluent; and a dispersant compound of the present application.

Another aspect of the present application is directed to fuel composition comprising a base fuel; and a dispersant compound of the present application.

Another aspect of the present application is directed to a method of reducing deposits in the fuel system of an internal combustion engine, the method comprising using as the fuel for the internal combustion engine a fuel composition of the present application, wherein a dispersant compound of the present application is present in the fuel in an amount sufficient to reduce the deposits in the fuel system, as compared to the amount of deposits in the fuel system operated in the same manner and using the same fuel composition except that the fuel composition is devoid of the dispersant compound.

Another aspect of the present application is directed to a method of dispersing soot, comprising providing to a combustion system a fuel composition of the present application. A dispersant compound of the present application is present in the fuel composition in an amount sufficient to maintain at least some soot in suspension in the base fuel for a period of time longer than if the base fuel did not contain the dispersant compound.

A fuel additive package composition comprising a diluent; and a dispersant compound of the present application.

Additional aspects and advantages of the disclosure will be set forth in part in the description which follows, and can be learned by practice of the disclosure. It is to be understood that both the foregoing general description and the following detailed description are exemplary and explanatory only and are not restrictive of the disclosure, as claimed.

DESCRIPTION OF THE EMBODIMENTS

The present application is directed to the preparation of novel dispersant compounds and their uses. In one aspect of the present application, the dispersant compounds comprise the reaction product of (i) a hydrocarbyl carbonyl compound, (ii) a polycarbonyl compound having at least three carbonyl acylating functions, and (iii) a primary amine moiety of a polyamine. The dispersant compounds of the present application have extended polar regions, which can result in one or more advantages, such as, for example, improved dispersant function in fuel and/or lubricating compositions.

In some aspects, the dispersant compounds of the present application are made by preparing a polyamine polyamide intermediate, which is reacted with a hydrocarbyl carbonyl compound. The intermediate can be prepared by reacting a polycarbonyl compound having at least three carbonyl acylating moieties with a primary amine moiety of a polyamine. Other suitable methods for forming the dispersant compounds of the present application may be employed, as will be discussed in greater detail below.

Polycarbonyl Compounds

The polycarbonyl reactant compounds used to form the polyamine polyamide intermediates of the present application can include any suitable organic compound that has at least three carbonyl acylating groups, and that is capable of reaction to form amides. In some embodiments, the polycarbonyl compound can include one or more tertiary nitrogen atoms. Examples of such polycarbonyl compounds include, but are not limited to, amine polycarboxylic acids or esters, of the following formula I:

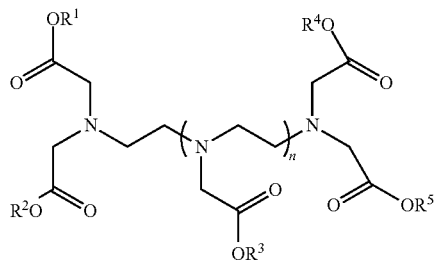

wherein n can range from 0 to about 10, and $R^1$, $R^2$, $R^3$, $R^4$ and $R^5$ are independently chosen from a hydrogen atom and $C_1$ to $C_{10}$ linear or branched alkyl groups, such as methyl, ethyl and butyl. Non-limiting examples of the carbonyl compounds of Formula I include ethylene diamine tetra acetic acid (EDTA), diethylene triamine pentaacetic acid, as well as methyl, ethyl, propyl and butyl esters of these acids.

In one embodiment of the compound of formula I, at least one or more of $R^1$, $R^2$, $R^3$, $R^4$ and $R^5$ are chosen to be $C_1$ to $C_{10}$ linear or branched alkyl groups. For example, the compound of formula I can be a mono, di, tri, or tetra ester of ethylene diamine tetra acetic acid. The ester can be formed by any suitable method. For example, an acid or salt of formula I, such as EDTA or a sodium salt of EDTA, can be reacted with an alcohol in the presence of an acid which can act as an esterification catalyst. Examples of suitable alcohols include methanol, ethanol, propanol and butanol. Examples of suitable esterification catalyst acids include sulfuric acid, methanesulfonic acid, toluenesulfonic acid, hydrogen chloride.

In other embodiments, the polycarbonyl compound can be a compound other than the compounds of formula I. For example, in one aspect, the polycarbonyl compound can be a carboxylic acid having at least three carbonyl acylating functions, or esters thereof, which does not contain a tertiary nitrogen, such as, citric acid or esters of citric acid.

Polyamine Compounds

In some aspects, the polyamine reactant used to form the polyamine polyamide intermediate of the present application can be a linear, branched or cyclic polyalkyleneamine having at least one primary amine moiety. For example, the polyamine can be a polyalkyleneamine of the following Formula II:

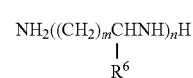

wherein $R^6$ can be a hydrogen atom or a low molecular weight alkyl group having from about 1 to about 6 carbon atoms, m can be an integer ranging from about 1 to about 3 and n can be an integer ranging from about 2 to about 10. Non-limiting examples of $R^6$ alkyl groups include methyl, ethyl, propyl or butyl.

Non-limiting examples of suitable polyamines include propylene diamine, butylene diamine, diethylene triamine (DETA), triethylene tetramine (TETA), tetraethylene pentamine (TEPA), pentaethylene hexamine (PEHA), hexaethyleneheptamine (HEHA), dipropylene triamine and tripropylene tetramine. The polyamines can include linear, branched or cyclic compounds, or mixtures thereof. In one aspect, the polyamine is a polyethyleneamine, such as DETA, TETA, TEPA, PEHA, and HEHA. In one aspect, the polyamine can be a copolymer of any one of the foregoing polyethyleneamines ranging in molecular weight from about 100 to about 600.

In some aspects, the polyamines can include mixtures of two or more polyamine compounds, such as mixtures of two or more compounds chosen from TEPA, PEHA, HEHA, and higher molecular weight polyethyleneamine products. In some aspect, the mixture can comprise heavy polyamines. A heavy polyamine is a mixture of polyalkyleneamines comprising small amounts of lower amine oligomers such as TEPA and PEHA but primarily oligomers with 7 or more nitrogen atoms, 2 or more primary amines per molecule, and more extensive branching than conventional amine mixtures.

Any suitable reaction conditions can be employed which result in the desired intermediate compound. In one aspect, the polycarbonyl compound can be heated to a temperature ranging from about 100° C. to about 125° C. in a relatively inert atmosphere, such as under vacuum or in nitrogen gas. The polyamine can then be mixed with the heated polycarbonyl. In this aspect, reaction times can range from about 1 hour to about 5 hours. The reaction can be run neat or with solvents. Any water or solvent can be removed to provide the desired polyamine polyamide intermediate.

The ratio of polycarbonyl reactant to polyamine reactant can be based upon the ratio of the carbonyl moieties to primary amine moieties in the reactants. This carbonyl to primary amine ratio can be any suitable ratio, such that there remains at least one unreacted primary amine moiety in the intermediate. In one embodiment, the ratio of polycarbonyl compounds to primary amine compounds can range from about 1:1 to about 1:5.

The resulting intermediate compound comprises an alkyl or alkylamine backbone having one or more polyamine polyamide groups, and optionally one or more carboxyl functional groups and/or carboxylate moieties. For example, the intermediate compound can be a compound of formula III,

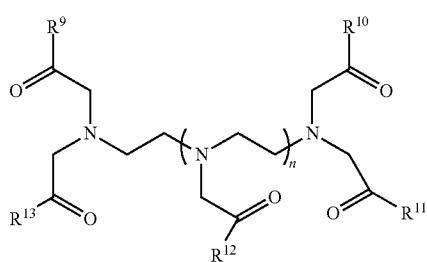

III where n ranges from 0 to 10, and $R^9$, $R^{10}$, $R^{11}$, $R^{12}$ and $R^{13}$ are independently chosen from a hydroxyl group, a polyamine group, or a polyamine salt group (e.g., $-O^{-+}H$-TEPA), with the proviso that at least one of $R^9$, $R^{10}$, $R^{11}$, $R^{12}$ and $R^{13}$ is a polyamine group. The polyamine groups and polyamine salt groups can be derived from any of the polyamine compounds described above. Examples of such groups include propylene diamine groups, butylene diamine groups, diethylene triamine (DETA) groups, triethylene tetramine (TETA) groups, tetraethylene pentamine (TEPA) groups, pentaethylene hexamine (PEHA) groups, hexaethyleneheptamine (HEHA) groups, dipropylene triamine groups and tripropylene tetramine groups, and salts of these groups. Where $R^9$, $R^{10}$, $R^{11}$, $R^{12}$ or $R^{13}$ is a polyamine group, a primary amine nitrogen atom of the polyamine links with the corresponding carbonyl acylating group of formula III to form an amide.

Hydrocarbyl Carbonyl Compound

The hydrocarbyl carbonyl reactant compound of the present application can be any suitable compound having a hydrocarbyl moiety and a carbonyl moiety, and that is capable of bonding with the polyamine polyamide intermediate compound to form the dispersant compounds of the present application. Non-limiting examples of suitable hydrocarbyl carbonyl compounds include, but are not limited to, hydrocarbyl substituted succinic anhydrides, hydrocarbyl substituted succinic acids, and esters of hydrocarbyl substituted succinic acids. Specific examples include such compounds as dodecenylsuccinic anhydrides, $C_{16-18}$ alkenyl succinic anhydride, and polyisobutenyl succinic anhydride (PIBSA). In some embodiments, the PIBSA may have a polyisobutylene portion with a molecular weight ranging from about 200 to about 6000 daltons and a vinylidene content ranging from about 4% to greater than about 90%. In some embodiments, the ratio of the number of carbonyl groups to the number of hydrocarbyl moieties in the hydrocarbyl carbonyl compound can range from about 1:1 to about 6:1.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, and sulfoxy);

(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

In some aspects, the hydrocarbyl carbonyl compound can be a polyalkylene succinic anhydride reactant having the following Formula IV:

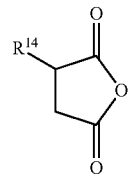

IV wherein $R^{14}$ is a hydrocarbyl moiety, such as for example, a polyolefin radical having a number average molecular weight of from about 350 to about 10,000 daltons. For example, the number average molecular weight of $R^{14}$ can range from about 1000 to about 5000 daltons as measured by GPC. Unless indicated otherwise, molecular weights in the present specification are number average molecular weights.

In some aspects, $R^{14}$ can be a polyolefin radical comprising one or more polymer units chosen from linear or branched alkenyl units. In some aspects, the alkenyl units can have from about 2 to about 10 carbon atoms. For example, the polyolefin radical can comprise one or more linear or branched polymer units chosen from ethylene radicals, propylene radicals, butylene radicals, pentene radicals, hexene radicals, octene radicals and decene radicals. In some aspects, $R^{14}$ can be a polyolefin radical in the form of, for example, a homopolymer, copolymer or terpolymer. For example, the polyolefin radical can be a copolymer of ethylene and propylene. In another example, the polyolefin radical is a homopolymer of polyisobutylene. The polyolefin compounds used to form the $R^{14}$ polyolefin radicals can be formed by any suitable methods, such as by conventional catalytic oligomerization of alkenes.

In some aspects, high reactivity polyisobutenes having relatively high proportions of polymer molecules with a terminal vinylidene group can be used to form the hydrocarbyl substituent. In one example, at least 4% of the total terminal olefinic double bonds in such high reactivity polyisobutenes can be a methylvinylidene isomer. In other examples, 50% or more of the total terminal olefinic double bonds can be methylvinylidene isomers, such as at least 70%. Well known high reactivity polyisobutenes are disclosed, for example, in U.S. Pat. No. 4,152,499, the disclosure of which is herein incorporated by reference in its entirety.

The hydrocarbyl carbonyl compounds can be made using any suitable method. Methods for forming hydrocarbyl carbonyl compounds are well known in the art. One example of a known method for forming a hydrocarbyl carbonyl compound comprises blending a polyolefin and maleic anhydride. The polyolefin and maleic anhydride reactants are heated to temperatures of, for example, about 150° C. to about 250° C., optionally, with the use of a catalyst, such as chlorine or peroxide.

The hydrocarbyl carbonyl compound can be combined with the polyamine polyamide intermediate under any suitable reaction conditions that will result in the desired dispersant compound of the present application. For example, the hydrocarbyl carbonyl can be heated to a temperature ranging from about 100° C. to about 160° C. under nitrogen. The polyamine polyamide intermediate can then be added. The reactant mixture can be stirred and heated at temperatures ranging from about 140° C. to about 200° C. under reduced pressure for about 2 hours to about 6 hours. The reaction can be run neat or with solvents and/or diluents, such as process oil. After the reaction is completed the mixture can be diluted with process oil and filtered to afford the desired dispersant.

In an alternative embodiment, the reaction of the polycarbonyl, polyamine, and hydrocarbyl carbonyl compounds may be carried out in a different order than is described above. For example, instead of reacting a polycarbonyl compound and a polyamine compound to form the above described polyamine polyamide intermediate, the hydrocarbyl carbonyl compounds described above can be reacted with the polyamine compounds described above to form a mono-succinimide amine intermediate. Examples of such mono-succinimide amine intermediates can be of the following formula V.

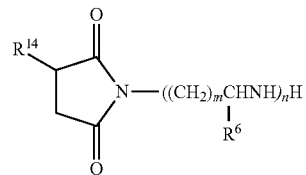

where $R^6$, $R^{14}$, m and n are as defined above.

The reaction of the hydrocarbyl carbonyl and polyamine compounds can be carried out under any conditions that will result in the desired mono-succinimide compounds. For example a 1:1 molar equivalent of a hydrocarbyl carbonyl compound and polyamine can be blended and heated to temperatures ranging from, for example, about 120° C. to about 250° C.

The mono-succinimide amine intermediate can then be reacted with the polycarbonyl ester compounds described above, such as the esters of formula I or esters of carboxylic acids, to form the desired dispersant compounds of the present application. The reaction can be carried out by blending any suitable amounts of the mono-succinimide amine intermediate and polycarbonyl ester compounds under suitable process conditions. For example, the ratio of mono-succinimide amine intermediate to polycarbonyl ester compound can range from about 2.7:1 to about 4:1. The reaction can be performed under conditions necessary to react an amine with an ester to form an amide bond. For example, the reaction can be performed neat or in a process oil at a temperature ranging from about 100° C. to about 180° C.

Polyamine Polyamide Succinimide Compounds

In some aspects, the dispersant compounds of the present application can comprise polyamine polyamide succinimide compounds. The polyamine polyamide succinimide dispersant compounds of the present application comprise an alkyl or alkylamine backbone having one or more polyamine polyamide succinimide groups, and optionally one or more carboxylate functional groups and/or polyamine polyamide succinimide salts. Non-limiting examples of the polyamine polyamide succinimide compounds include compounds of formula VI:

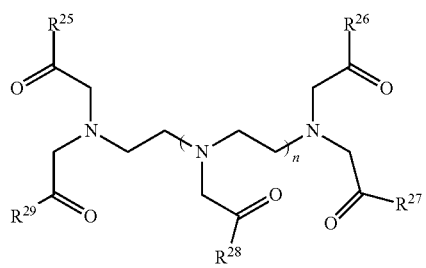

wherein n ranges from 0 to 10, and $R^{25}$, $R^{26}$, $R^{27}$, $R^{28}$ and $R^{29}$ are independently chosen from a polyamine succinimide group or a polyamine succinimide group salt (e.g., —O$^{-+}$H-TEPA succinimide group), with the proviso that at least one of $R^{25}$, $R^{26}$, $R^{27}$, $R^{28}$ and $R^{29}$ is a polyamine succinimide group.

In one aspect of the application, $R^{25}$, $R^{26}$, $R^{27}$, $R^{28}$ and $R^{29}$ are independently chosen from polyamine succinimide groups of the formula VII, and salts thereof:

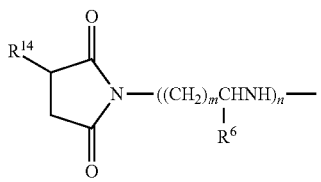

VII wherein $R^6$, $R^{14}$, m and n are defined as above. Non-limiting examples of such polyamine succinimide groups include propylene diamine succinimide groups, butylene diamine succinimide groups, diethylene triamine (DETA) succinimide groups, triethylene tetramine (TETA) succinimide groups, tetraethylene pentamine (TEPA) succinimide groups, pentaethylene hexamine (PEHA) succinimide groups, hexaethyleneheptamine (HEHA) succinimide groups, dipropylene triamine succinimide groups and tripropylene tetramine succinimide groups, and salts of these groups.

The dispersant compounds of the present application are useful as dispersants in lubricant compositions. Accordingly, one aspect of the present application relates to a lubricating oil composition comprising a major amount of an oil of lubricating viscosity and an amount of a dispersant compound of the present application sufficient to provide dispersancy. The term "major amount" as used herein means an amount greater than or equal to 50% by weight relative to the total weight of the composition.

When the dispersant compounds of this application are used in lubricant compositions, they can be present in any suitable amount. In one example, the dispersant compounds can be present in an amount of from about 0.1 to about 20% by weight of the total composition, such as from about 0.5 to about 15% by weight, and in another example, from about 1 to about 7% by weight.

The lubricating compositions disclosed herein can comprise a base oil. Base oils suitable for use in formulating the disclosed compositions can be selected from, for example, synthetic or mineral oils, or mixtures thereof.

The base oil can be present in a major amount, wherein "major amount" is understood to mean greater than or equal to 50% by weight of the lubricant composition, such as from about 80% to about 98% by weight of the lubricant composition. The base oil typically has a viscosity of, for example, from about 2 to about 15 cSt and, as a further example, from about 2 to about 10 cSt at 100° C.

Non-limiting examples of mineral oils suitable as base oils include animal oils and vegetable oils (e.g., castor oil, lard oil) as well as other mineral lubricating oils such as liquid petroleum oils and solvent treated or acid-treated mineral lubricating oils of the paraffinic, naphthenic or mixed paraffinic-naphthenic types. Oils derived from coal or shale are also suitable. Further, oils derived from a gas-to-liquid process are also suitable.

Non-limiting examples of synthetic oils include hydrocarbon oils such as polymerized and interpolymerized olefins (e.g., polybutylenes, polypropylenes, propylene isobutylene copolymers, etc.); polyalphaolefins such as poly(1-hexenes), poly-(1-octenes), poly(1-decenes), etc. and mixtures thereof; alkylbenzenes (e.g., dodecylbenzenes, tetradecylbenzenes, di-nonylbenzenes, di-(2-ethylhexyl)benzenes, etc.); polyphenyls (e.g., biphenyls, terphenyl, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that can be used. Such oils are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_{3-8}$ fatty acid esters, or the $C_{13}$ Oxo acid diester of tetraethylene glycol.

Another class of synthetic oils that can be used includes the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_{5-12}$ monocarboxylic acids and polyols and polyol ethers such as neopentyl glycol, trimethylol propane, pentaerythritol, dipentaerythritol, tripentaerythritol, etc.

Hence, the base oil used to make the compositions as described herein can be selected from any of the base oils in Groups I-V as specified in the American Petroleum Institute (API) Base Oil Interchangeability Guidelines. Such base oil groups are as follows:

Group I contain less than 90% saturates and/or greater than 0.03% sulfur and have a viscosity index greater than or equal to 80 and less than 120; Group II contain greater than or equal to 90% saturates and less than or equal to 0.03% sulfur and have a viscosity index greater than or equal to 80 and less than 120; Group III contain greater than or equal to 90% saturates and less than or equal to 0.03% sulfur and have a viscosity index greater than or equal to 120; Group IV are polyalphaolefins (PAO); and Group V include all other basestocks not included in Group I, II, III or IV.

The test methods used in defining the above groups are ASTM D2007 for saturates; ASTM D2270 for viscosity index; and one of ASTM D2622, 4294, 4927 and 3120 for sulfur.

Group IV basestocks, i.e. polyalphaolefins (PAO) include hydrogenated oligomers of an alpha-olefin, the most important methods of oligomerisation being free radical processes, Ziegler catalysis, and cationic, Friedel-Crafts catalysis.

The polyalphaolefins typically have viscosities in the range of 2 to 100 cSt at 100° C., for example 4 to 8 cSt at 100° C. They can, for example, be oligomers of branched or straight chain alpha-olefins having from about 2 to about 30 carbon atoms; non-limiting examples include polypropenes, polyisobutenes, poly-1-butenes, poly-1-hexenes, poly-1-octenes and poly-1-decene. Included are homopolymers, interpolymers and mixtures.

Regarding the balance of the basestock referred to above, a "Group I basestock" also includes a Group I basestock with which basestock(s) from one or more other groups can be admixed, provided that the resulting admixture has characteristics falling within those specified above for Group I basestocks.

Exemplary basestocks include Group I basestocks and mixtures of Group II basestocks with Group I basestock.

Basestocks suitable for use herein can be made using a variety of different processes including but not limited to distillation, solvent refining, hydrogen processing, oligomerisation, esterification, and re-refining.

The base oil can be an oil derived from Fischer-Tropsch synthesized hydrocarbons. Fischer-Tropsch synthesized hydrocarbons can be made from synthesis gas containing $H_2$ and CO using a Fischer-Tropsch catalyst. Such hydrocarbons typically require further processing in order to be useful as the base oil. For example, the hydrocarbons can be hydroisomerized using processes disclosed in U.S. Pat. No. 6,103,099 or 6,180,575; hydrocracked and hydroisomerized using processes disclosed in U.S. Pat. No. 4,943,672 or 6,096,940; dewaxed using processes disclosed in U.S. Pat. No. 5,882,505; or hydroisomerized and dewaxed using processes disclosed in U.S. Pat. No. 6,013,171; 6,080,301; or 6,165,949.

Unrefined, refined and rerefined oils, either mineral or synthetic (as well as mixtures of two or more of any of these) of the type disclosed hereinabove can be used in the base oils. Unrefined oils are those obtained directly from a mineral or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils, where the processes are applied to refined oils which have been already used in service. Such rerefined oils are also known as reclaimed or reprocessed oils and often are additionally processed by techniques directed to removal of spent additives, contaminants, and oil breakdown products.

The lubricant compositions of the present application can be used in any engine or other combustion systems or mechanical devices that may benefit therefrom. For example, the lubricant compositions can be suitable for use in the crank case of an internal combustion engine.

In some embodiments, the dispersant compounds of the present application can be added to the lubricant composition in the form of a lubricant additive package. Lubricant additive packages include concentrates dissolved in a diluent, such as mineral oil, synthetic hydrocarbon oils, and mixtures thereof. When blended with the base oil, these concentrate additive compositions can provide an effective concentration of the additives in the base oil. The amount of the dispersant compounds of the present application in the lubricant additive packages may vary from about 5 wt % to about 75 wt % of the concentrate additive composition, such as from about 5 wt % to about 50 wt %.

The lubricant additive package compositions and finished lubricants of the present application may contain other additional additives. Examples of such additional additives include dispersants other than the dispersants of the present application, detergents, anti-wear agents, supplemental antioxidants, viscosity index improvers, pour point depressants, corrosion inhibitors, rust inhibitors, foam inhibitors, and friction modifiers. Such additives are well known in the art, and choosing effective amounts of additional additives in lubricant compositions would be within the ordinary skill of the art.

In one aspect, the present application is directed to a method of reducing deposits on a lubricated surface, wherein said method comprises using as the lubricating oil for said surface a lubricating oil containing the dispersant compound of the present invention. The dispersant compound can be present in an amount sufficient to reduce the amount of deposits on the surface, as compared to the amount of deposits that would be formed on the surface if it were subjected to the same operating conditions and using the same lubricating oil, except that the oil was devoid of the dispersant compound. Representative examples of the deposits that may be reduced using the compositions of the present invention include piston deposits, ring land deposits, crown land deposits and top land deposits.

In another aspect, the present application is directed to a method for improving the suspension of sludge in a lubricating oil. The method comprises providing to a combustion system the lubricating oils of the present application, wherein the dispersant compound is present in an amount sufficient to maintain at least some sludge in suspension in the oil for a period of time longer than if the oil did not contain the dispersant compound.

The dispersant compounds of the present application are also useful as dispersants in fuels. Thus, another aspect of the present application is a fuel composition comprising a major amount of a fuel and a minor amount of dispersant compounds of the present application sufficient to provide a desired dispersancy. The concentration of the additive in a fuel is dependent upon a variety of factors, including the type of fuel used, the presence of other dispersants or other additives, and the like. Non-limiting example concentrations can range from about 10 to about 10,000 weight parts per million, or from about 30 to about 5,000 weight parts per million.

The base fuels used in formulating the fuel compositions of the present invention include any base fuels suitable for use in the operation of spark-ignition or compression-ignition internal combustion engines such as diesel fuel, jet fuel, kerosene, leaded or unleaded motor and aviation gasolines, and so-called reformulated gasolines which can contain both hydrocarbons of the gasoline boiling range and fuel-soluble oxygenates, such as alcohols, ethers and other suitable oxygen-containing organic compounds. Examples of oxygenates suitable for use in the present application include methanol, ethanol, isopropanol, t-butanol, mixed $C_1$ to $C_5$ alcohols, methyl tertiary butyl ether, tertiary amyl methyl ether, ethyl tertiary butyl ether and mixed ethers. Oxygenates, when used, can be present in the base fuel in an amount below, for example, about 25% by volume. In some embodiments, the oxygenates can be present in an amount that provides an oxygen content in the overall fuel in the range of about 0.5 to about 5 percent by volume.

The base fuels used in formulating the fuel compositions of the present invention can include, for example, compression ignition fuels having a sulfur content of up to about 0.2% by weight, such as up to about 0.05% by weight, as determined by the test method specified in ASTM D 2622-98. In some embodiments, suitable compression-ignition fuels for use in the present invention are low sulfur content diesel fuels.

In yet another aspect of the present application, the dispersant compounds are useful as fuel additive concentrates. The fuel concentrates can comprise an inert stable organic solvent for a diluent and from about 5 to 50 weight percent of a dispersant compound of the present application. Non-limiting examples of suitable diluents include benzene, toluene, xylene or higher boiling aromatics.

In one aspect, the present application is directed to a method of reducing deposits in the fuel system of an internal combustion engine, the method comprising using as the fuel for the internal combustion engine the fuel compositions described above. The dispersant compounds of the present application can be present in the fuel in an amount sufficient to reduce the deposits in the fuel system. Deposits may be reduced as compared to the amount of deposits that would occur in the same fuel system operated in the same manner and using the same fuel composition, if the fuel composition were devoid of the dispersant compound.

In one aspect, the present application is directed to a method of dispersing soot in a base fuel. The method comprises providing to a combustion system the fuel compositions of the present application, wherein the dispersant compound is present in the base fuel in an amount sufficient to maintain at least some soot in suspension in the base fuel for a period of time longer than if the base fuel did not contain the dispersant compound.

The following Examples are offered to specifically illustrate this invention. These Examples and illustrations are not to be construed in any way as limiting the scope of this invention.

EXAMPLES

Example 1A

To a 1 L resin kettle was charged 43.8 g of ethylenediamine tetraacetic acid and 370 mL of water. The resulting suspension was stirred and heated at 100° C. TEPA (113.4 g) was added via an addition funnel, and the reaction mixture was stirred and heated under nitrogen for 3 hours. The suspension turned to a yellow solution upon addition of the amine. The water was removed in vacuo from the reaction mixture to afford 156 g of yellow viscous oil. This intermediate was diluted with 100 g of water and transferred to a jar.

A proposed intermediate for the process of Example 1A is shown as the product of the reaction illustrated below:

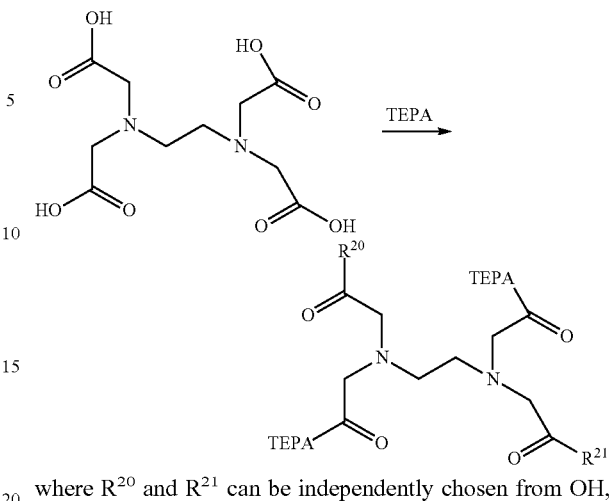

where $R^{20}$ and $R^{21}$ can be independently chosen from OH, TEPA, and TEPA salt ($O^{-+}H$-TEPA).

Example 1B

To a 3 L resin kettle equipped with an overhead stirrer was charged 951 g of a 1250 Mn PIBSA. The PIBSA was heated to 160° C. and stirred under nitrogen. Then 248.1 g of the intermediate from Example 1A was added via an addition funnel over a 1 hour period. The reaction mixture was stirred and heated for 3 hours under reduced pressure. The reaction mixture was diluted with 880 g of process oil and filtered to afford 1800 g of the desired product.

A proposed reaction for the process of Example 1B is illustrated below:

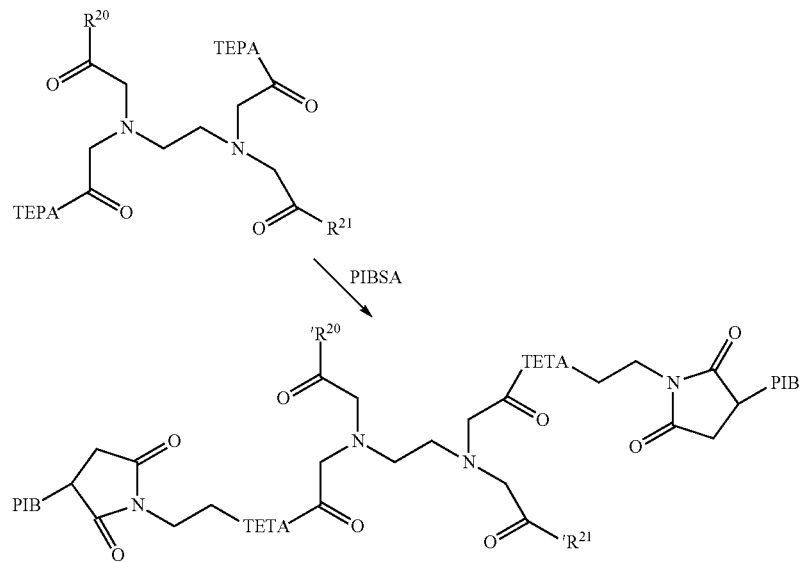

where '$R^{20}$ and '$R^{21}$ can be independently chosen from TEPA succinimide and TEPA succinimide salt.

Example 2

The additive of Example 1B was blended into a passenger car motor oil formulation utilizing other components, including metal-containing sulfonates, zinc dithiophosphate wear inhibitors, sulfur containing antioxidants, diaryl amine and phenolic antioxidants, oleate and molybdenum friction modifiers, a pour point depressant, a viscosity index improver (HiTEC®5751) and a lubricating base oil. These other components were in concentrations typically found in fully formulated multi-grade passenger car motor oils.

The kinematic viscosity at 100° C. (KV100) (mm²/s) and cold cranking simulator viscosity at 30° C. (CCS-30) (centipoise) were determined and the results are shown in Table 1 below.

TABLE 1

5W 30 Blend Study Results

| Dispersant | KV100 | CCS-30 |
|---|---|---|
| Example 1B | 11.28 | 5895 |

Example 3

In Table 2 below, the sludge containing properties of a lubricant containing the dispersant of example 1B, as described above, and a comparative lubricant containing a commercially available dispersant were compared using the Sequence VG engine test (an industry dispersant sludge test), to determine average engine sludge ("AES"), rocker cover sludge ("RCS"), piston skirt varnish ("PSV"), and average engine varnish ("AEV"). The lubricants used were fully formulated lubricants. In each sample, the ingredients of the lubricant are exactly the same except for the dispersant.

The Sequence VG engine sludge and varnish deposit test is a fired engine-dynamometer test that evaluates the ability of a lubricant to minimize the formation of sludge and varnish deposits. The test method was a cyclic test, with a total running duration of 216 hours, consisting of 54 cycles of 4 hours each. The test engine was a Ford 4.6 L, spark ignition, four stroke, eight cylinder "V" configuration engine. Features of this engine include dual overhead camshafts, a cross-flow fast burn cylinder head design, two valves per cylinder, and electronic port fuel injection. A 90-minute break-in schedule was conducted prior to each test, since a new engine build is used for each test. Upon test completion, the engine was disassembled and rated for sludge. Average engine sludge was calculated for each sample.

The results of this testing are shown in Table 2. The pass limits for each performance measure are also indicated in the table.

TABLE 2

Sequence VG Engine Test Results

| Dispersant Code | AES | RCS | AEV | PSV |
|---|---|---|---|---|
| Example 1B | 8.91 | 9.54 | 9.22 | 8.02 |
| Comparative | 7.91 | 9.25 | 8.90 | 7.64 |
| Pass limits | 7.80 | 8.00 | 8.90 | 7.50 |

As shown from Table 2 above, the lubricant containing the dispersant of Example 1B not only passed each performance measure, but resulted in higher AES, RCS, AEV and PSV test scores than the Comparative Example A. The results of this test indicate improved performance of the dispersant of the present application.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "an acid" includes two or more different acids. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A process for forming a dispersant compound comprising:
   (i) reacting a polycarbonyl compound of formula I having at least three carbonyl functions with a primary amine moiety of a polyamine of formula II to form a polyamine polyamide intermediate; and
   (ii) reacting the polyamine polyamide intermediate with a hydrocarbyl carbonyl compound of formula IV, wherein formula I is:

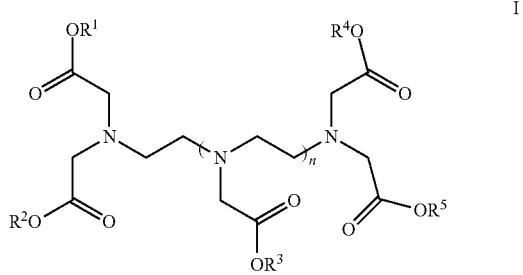

where n ranges from 0 to 4, and where $R^1$, $R^2$, $R^3$, $R^4$ and $R^5$ are independently chosen from a hydrogen atom and $C_1$ to $C_{10}$ linear or branched alkyl groups,
wherein formula II is:

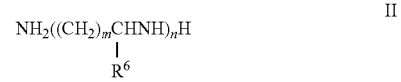

wherein $R^6$ is a hydrogen atom or an alkyl group having from 1 to 6 carbon atoms, m is an integer ranging from 1 to 3, and n is an integer ranging from 2 to 10, wherein a mole ratio of polycarbonyl compound to polyamine of formula II ranges from about 1:3 to about 1:5 to provide the polyamine polyamide dispersant intermediate compound of formula III,

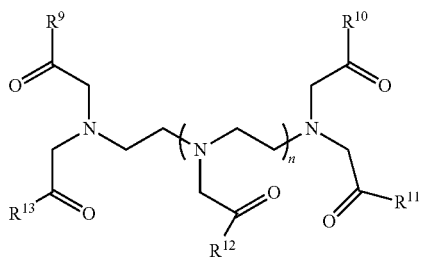

where n ranges from 0 to 4, and $R^9$, $R^{10}$, $R^{11}$, $R^{12}$ and $R^{13}$ are independently chosen from OH, a polyamine group, or a amine salt of the polyamine group, with the proviso that at least three of $R^9$, $R^{10}$, $R^{12}$ and $R^{13}$ are polyamine groups, and wherein formula IV is:

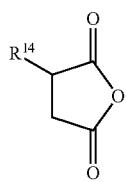

wherein $R^{14}$ is a hydrocarbyl group.

2. The process of claim 1, wherein $R^{14}$ is polyisobutene.

3. A polyamine polyamide dispersant intermediate compound formed by reacting a polycarbonyl compound of formula I having at least three carbonyl functions with a primary amine moiety of a polyamine of formula II, wherein formula I is:

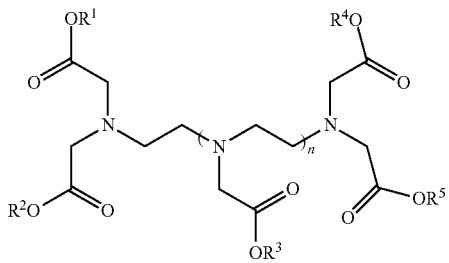

where n ranges from 0 to 4, and where $R^1$, $R^2$, $R^3$, $R^4$ and $R^5$ are independently chosen from a hydrogen atom and $C_1$ to $C_{10}$ linear or branched alkyl groups, and wherein formula II is:

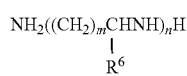

wherein $R^6$ is a hydrogen atom or an alkyl group having from 1 to 6 carbon atoms, m is an integer ranging from 1 to 3, and n is an integer ranging from 2 to 10, wherein a mole ratio of polycarbonyl compound to primary amine compound ranges from about 1:3 to about 1:5 to provide the polyamine polyamide dispersant intermediate compound of formula III,

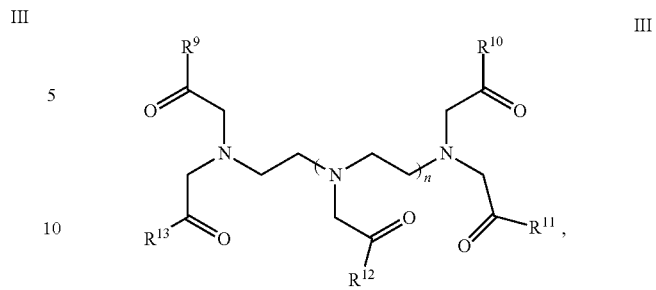

where n ranges from 0 to 4, and $R^9$, $R^{10}$, $R^{11}$, $R^{12}$ and $R^{13}$ are independently chosen from OH, a polyamine group, or a salt of the polyamine group, with the proviso that at least one of $R^9$, $R^{10}$, $R^{11}$, $R^{12}$ and $R^{13}$ is a polyamine group.

4. The polyamine polyamide dispersant intermediate compound claim 3, wherein the polyamine groups are selected from the group consisting of diethylene triamine (DETA) groups, triethylene tetramine (TETA) groups, tetraethylene pentamine (TEPA) groups, pentaethylene hexamine (PEHA) groups, hexaethyleneheptamine (HEHA) groups, dipropylene triamine groups and tripropylene tetramine groups, and salts of these groups.

5. A method of forming a polyamine polyamide intermediate compound, the method comprising reacting a polycarbonyl compound of formula I having at least three carbonyl acylating functions with a primary amine moiety of a polyamine of formula II wherein formula I is:

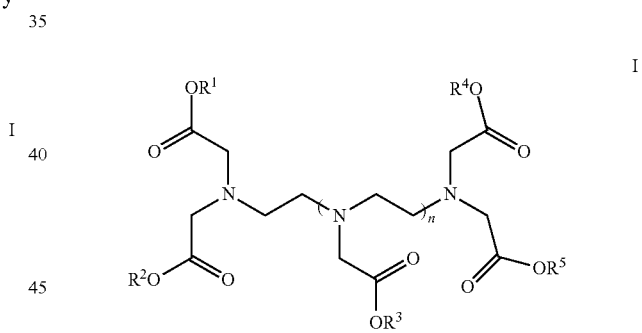

where n ranges from 0 to 4, and where $R^1$, $R^2$, $R^3$, $R^4$ and $R^5$ are independently chosen from a hydrogen atom and $C_1$ to $C_{10}$ linear or branched alkyl groups, and wherein formula II is:

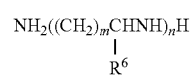

wherein $R^6$ is a hydrogen atom or an alkyl group having from 1 to 6 carbon atoms, m is an integer ranging from 1 to 3, and n is an integer ranging from 2 to 10, wherein a mole ratio of polycarbonyl compound to polyamine of formula II ranges from about 1:3 to about 1:5 to provide the polyamine polyamide dispersant intermediate compound of formula III,

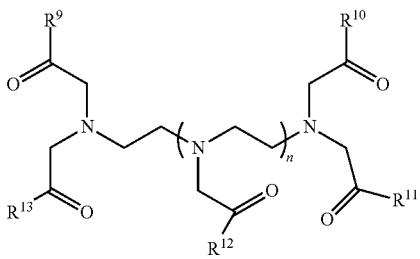

here n ranges from 0 to 4, and R$^9$, R$^{10}$, R$^{11}$, R$^{12}$ and R$^{13}$ are independently chosen from OH, a polyamine group, or a amine salt of the polyamine group, with the proviso that at least three of R$^9$, R$^{10}$, R$^{11}$, R$^{12}$ and R13 are polyamine groups.

6. The method of claim 5, wherein the polycarbonyl compound is chosen from ethylene diamine tetra acetic acid, diethylene triamine pentaacetic acid and esters of these acids.

7. The method of claim 5, wherein the polyamine is selected from the group consisting of , diethylene triamine (DETA), triethylene tetramine (TETA), tetraethylene pentamine (TEPA), pentaethylene hexamine (PEHA), hexaethyleneheptamine (HEHA), dipropylene triamine and tripropylene tetramine.

8. A process for forming a dispersant compound comprising:
  (i) reacting a hydrocarbyl carbonyl compound of formula IV with a primary amine moiety of a polyamine of formula II to form a mono-succinimide amine intermediate; and
  (ii) reacting the mono-succinimide amine intermediate with a polycarbonyl compound of formula I having at least three carbonyl functions
  wherein the polycarbonyl compound is a compound of formula I:

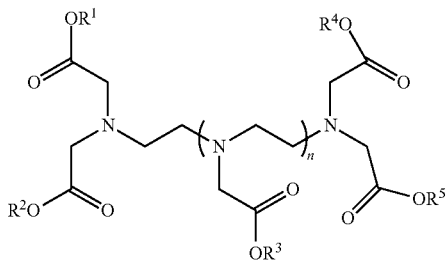

where n ranges from 0 to 4, and where R$^1$, R$^2$, R$^3$, R$^4$ and R$^5$ are independently chosen from a hydrogen atom and C$_1$ to C$_{10}$ linear or branched alkyl groups, wherein the polyamine is a compound of formula II:

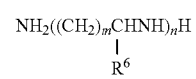

wherein R$^6$ is a hydrogen atom or an alkyl group having from 1 to 6 carbon atoms, m is an integer ranging from 1 to 3, and n is an integer ranging from 2 to 10, and wherein the hydrocarbyl carbonyl compound is a compound of the following formula IV:

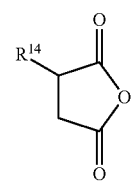

wherein R$^{14}$ is a hydrocarbyl group.

9. The process of claim 8, wherein the hydrocarbyl carbonyl compounds are chosen from hydrocarbyl substituted succinic anhydrides, hydrocarbyl substituted succinic acids, and esters of hydrocarbyl substituted succinic acids.

10. The process of claim 8, wherein R$^{14}$ is polyisobutene.

* * * * *